United States Patent
Yotani et al.

(10) Patent No.: US 9,970,908 B2
(45) Date of Patent: May 15, 2018

(54) GRADIENT LIQUID FEED DEVICE FOR SAMPLE ANALYZER

(71) Applicant: Sekisui Medical Co., Ltd., Tokyo (JP)

(72) Inventors: Takuya Yotani, Tokyo (JP); Hiroaki Taira, Tokyo (JP); Takayuki Oka, Tokyo (JP); Hideki Muraki, Tokyo (JP)

(73) Assignee: Sekisui Medical Co., Ltd. (JP)

( * ) Notice: Subject to any disclaimer, the term of this patent is extended or adjusted under 35 U.S.C. 154(b) by 131 days.

(21) Appl. No.: 14/905,472

(22) PCT Filed: Jul. 17, 2014

(86) PCT No.: PCT/JP2014/069106
§ 371 (c)(1),
(2) Date: Jan. 15, 2016

(87) PCT Pub. No.: WO2015/008845
PCT Pub. Date: Jan. 22, 2015

(65) Prior Publication Data
US 2016/0153942 A1    Jun. 2, 2016

(30) Foreign Application Priority Data

Jul. 17, 2013 (JP) ................................. 2013-148369

(51) Int. Cl.
*G01N 30/34* (2006.01)
*G01N 30/88* (2006.01)
(Continued)

(52) U.S. Cl.
CPC ............. *G01N 30/34* (2013.01); *G01N 30/16* (2013.01); *G01N 30/88* (2013.01); *G01N 33/491* (2013.01);
(Continued)

(58) Field of Classification Search
CPC ...................................................... G01N 30/34
(Continued)

(56) References Cited

U.S. PATENT DOCUMENTS 5,450,743 A    9/1995 Buote
6,012,487 A    1/2000 Hauck
(Continued)

FOREIGN PATENT DOCUMENTS

EP    2345896 A1    7/2011
JP    S56-058454    5/1981
(Continued)

OTHER PUBLICATIONS

International Search Report for Application No. PCT/JP2014/069106 dated Oct. 21, 2014.
(Continued)

*Primary Examiner* — Manish S Shah
*Assistant Examiner* — Jean Morello
(74) *Attorney, Agent, or Firm* — Lerner, David, Littenberg, Krumholz & Mentlik, LLP

(57) ABSTRACT

A gradient liquid feed device allows reduction in size of a high performance liquid chromatography type sample analyzer. The gradient liquid feed device includes a plurality of carrier liquid reservoir tanks configured to store carrier liquids of mutually different compositions, a plurality of single plunger pumps capable of drawing and discharging the carrier liquid from the plurality of carrier liquid reservoir tanks, a mixer configured to mix the carrier liquids discharged from the plurality of liquid feed pumps and feed the mixed carrier liquid, and a pulse damper in communication with the mixer and configured to absorb pulsation that may occur during liquid feeding. The single plunger pumps have a function for variably setting a length of stroke for drawing and discharging the carrier liquid and a function for variably setting a ratio between the carrier liquid drawing time and the carrier liquid discharge time.

5 Claims, 1 Drawing Sheet

(51) Int. Cl.
*G01N 30/16* (2006.01)
*G01N 33/49* (2006.01)
*G01N 30/02* (2006.01)

(52) U.S. Cl.
CPC . *G01N 2030/027* (2013.01); *G01N 2030/347* (2013.01); *G01N 2030/8822* (2013.01)

(58) Field of Classification Search
USPC ........................................................ 73/61.55
See application file for complete search history.

(56) References Cited

U.S. PATENT DOCUMENTS

| | | |
|---|---|---|
| 2004/0108273 A1 | 6/2004 | Richardson et al. |
| 2011/0189715 A1* | 8/2011 | Likuski .............. G01N 35/1095 435/29 |
| 2015/0090345 A1* | 4/2015 | Olovsson ............ F16K 11/0743 137/15.06 |

FOREIGN PATENT DOCUMENTS

| | | |
|---|---|---|
| JP | H0460456 A | 2/1992 |
| JP | H09-264888 A | 10/1997 |
| JP | 2001074755 A | 3/2001 |
| JP | 2002303613 A | 10/2002 |
| JP | 2003-107065 A | 4/2003 |
| JP | 2003107069 A | 4/2003 |
| JP | 2006509214 A | 3/2006 |
| JP | 2011226914 A | 11/2011 |

OTHER PUBLICATIONS

Extended European Search Report for Application No. 14826856.8 dated Dec. 1, 2016, 11 pages.
Chinese Office Action and Search Report for Application No. 201480051314.2 dated Dec. 22, 2016.

* cited by examiner

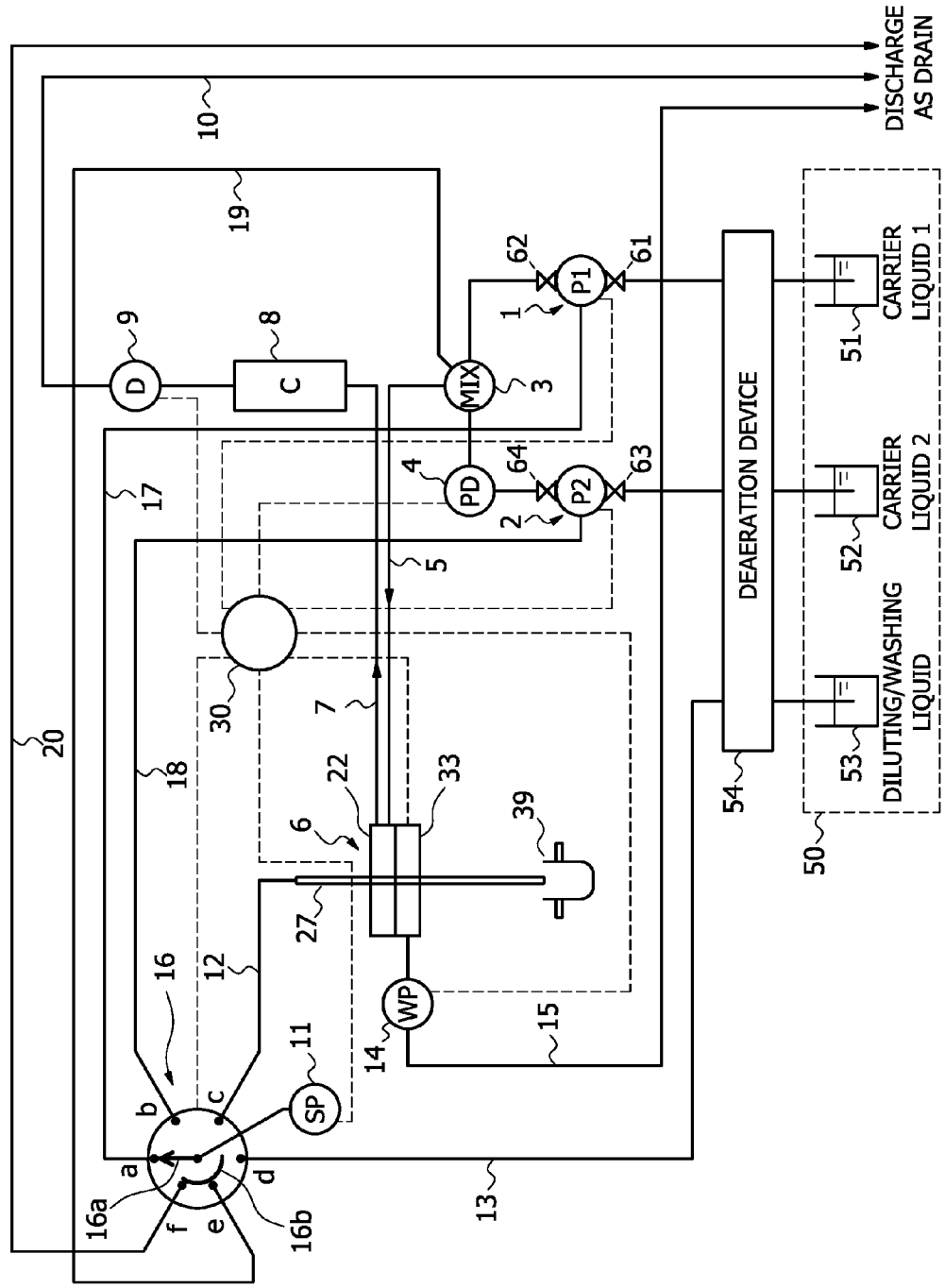

GRADIENT LIQUID FEED DEVICE FOR SAMPLE ANALYZER

CROSS-REFERENCE TO RELATED APPLICATIONS

The present application is a national phase entry under 35 U.S.C. § 371 of International Application No. PCT/JP2014/069106 filed Jul. 17, 2014, published in Japanese, which claims priority from Japanese Patent Application No. 2013-148369 filed Jul. 17, 2013, all of which are hereby incorporated herein by reference.

TECHNICAL FIELD

The present invention relates to a gradient liquid feed device capable of changing a composition of a carrier liquid (the content of an organic solvent, a salt concentration, and the like) during feeding of the carrier liquid (eluent) carried out in a high-performance liquid chromatography (HPLC) type sample analyzer, and more specifically relates to a small-size high-pressure linear gradient liquid feed device. The present invention further relates to a sample analyzer that uses the gradient liquid feed device and to a hemoglobin component measurement method.

BACKGROUND ART

In an HPLC type sample analyzer (hereinafter also simply referred to as a "sample analyzer"), in order to improve the sample separation capability and reduce the analysis time, often used is a gradient liquid feed device, which changes the composition of a carrier liquid (properties of the carrier liquid, such as the mixture ratio of a plurality of carrier liquids, the concentration of a reagent used for separation and elution of an analysis subject, the pH of the carrier liquid, and the like) in accordance with the passage of time.

Such a gradient liquid feed device includes a linear gradient liquid feed device, which changes the composition of a carrier liquid linearly or curvilinearly as time progresses, and a step gradient liquid feed device, which is a simple type device that changes the composition of a carrier liquid in a stepwise manner.

The linear gradient liquid feed devices include a low-pressure gradient type device which uses one low-pulsation pump that uses two or more plungers (e.g., a double plunger pump) and switches between a plurality of carrier liquids of different compositions by using a valve (an electromagnetic valve) provided on the side of a drawing port of the pump (see Patent Document 1, for example) and a high-pressure gradient type device which uses a plurality of low-pulsation pumps using two or more plungers in correspondence with the respective plurality of carrier liquids, which are integrated into one path on their discharge port side, and variably changes the flow rate of the respective pump (see Patent Document 2, for example).

Note that the term "flow rate" herein refers to a volumetric flow rate, which can be expressed as a multiplication of a cross section area of a fluid by a speed of flow (flow velocity) of the fluid.

REFERENCE DOCUMENT LIST

Patent Documents

Patent Document 1: Japanese Patent Application Laid-open Publication No. H09-264888

Patent Document 2: Japanese Patent Application Laid-open Publication No. 2002-303613

SUMMARY OF THE INVENTION

Problems to be Solved by the Invention

Of the two types of linear gradient type devices, the low-pressure gradient type device is used when the flow rate of a carrier liquid is high because the responsiveness of a gradient is low when the flow rate of a carrier liquid is low. In the present invention, the term "responsiveness of gradient" refers to the level of actually achieved change in the composition of a carrier liquid in relation to the expected change in the composition of the carrier liquid.

On the other hand, because the responsiveness of gradient is high in a high-pressure gradient type device, such a high-pressure gradient type device is primarily used when the flow rate of a carrier liquid is low. The high-pressure gradient type device enables ideal control of gradient; however, the costs are high because the size of the device may be large due to the use of a plurality of low-pulsation pumps each using two or more plungers.

As discussed above, in a linear gradient liquid feed device, pumps that use two or more plungers are used and no single plunger pump is used. This is because a sensitive analysis cannot be carried out with a single plunger pump due to a great pulsation which occurs because in the single plunger pump the carrier liquid is not discharged in a carrier liquid drawing step, and the time taken for drawing the carrier liquid may become long when the flow rate is low.

More specifically, for a cam type plunger pump, the cam is designed so that the time for the drawing step within one cycle of the reciprocating motion of the plunger may become as short as possible and so that most of the time for one cycle is used for the discharge step. However, because the ratio between the drawing time and the discharge time is constant, the drawing time may become longer when the speed of reciprocation of the plunger is decreased, and thus, the flow rate is low. Note that when the time in which the carrier liquid is not discharged is long, the change in the composition of the carrier liquid is adversely affected. In addition, as the number of times of cycle of drawing and discharge operations per unit time becomes higher, fluctuation of the flow velocity becomes smaller, and thus, effects from the pulsation will become smaller in the case of liquid feeding at a high flow rate, whereas in the case of liquid feeding at a low flow rate, the pulsation may become greater because the number of times of cycles of drawing and discharge operations per unit time decreases due to the lower speed of reciprocation of the plunger.

Under these circumstances, in HPLC type sample analyzers in actual use, in order to limit the device costs and the device size within a desired range, although the sample separation capability and the analysis time may be partially sacrificed, a step gradient liquid feed device is often used that uses one single plunger pump switches between a plurality of carrier liquids of different compositions on the drawing side of the pump by using a valve (an electromagnetic valve), and eliminates pulsation by using a pulse damper to feed the liquid.

In other words, a linear high-pressure gradient liquid feed device which uses a single plunger pump, in which the level of pulsation is low and which has a sufficient responsiveness of gradient even during feeding of carrier liquid at a low flow rate, has not been put into practical use yet.

The present invention has been devised in consideration of these circumstances, and an object of the present invention is to provide a low-cost, small-size linear high-pressure gradient liquid feed device with a high responsiveness of a gradient as a gradient device for use in an HPLC type sample analyzer without sacrificing the sample separation capability and the analysis time.

Means for Solving the Problems

In order to solve the above-described problem, the inventors of the present invention have found that a gradient liquid feed device for an HPLC type sample analyzer may include a plurality of carrier liquid reservoir tanks for storing carrier liquids of mutually different compositions, a plurality of single plunger pumps capable of drawing and discharging carrier liquid from each of the plurality of carrier liquid reservoir tank, a mixer configured to mix the carrier liquids discharged from the plurality of single plunger pumps together and feeds the mixed carrier liquids, and a pulse damper which is in communication with the mixer and configured to absorb pulsation that may occur during liquid feeding, and that in the gradient liquid feed device, the single plunger pump includes at least one, or preferably both, of a function for variably setting a length of stroke for drawing and discharging the carrier liquid and a function for variably setting a ratio between carrier liquid drawing time and carrier liquid discharge time.

In addition, the inventors of the present invention have found that in order to further improve the responsiveness of gradient, at least one pulse damper may be installed in a flow path provided between the single plunger pump and the mixer.

In addition, the inventors of the present invention have found that when the valve disclosed in Japanese Patent Application No. 2013-148183 (PCT/JP2014/61256) is used, air in the cylinder chamber can be released only by an operation of the liquid feeding device even when the length of the stroke by a single plunger pump for drawing and discharging the carrier liquid is short and poor liquid feeding may not occur in the pump, and thus have completed the present invention.

In addition, the inventors of the present invention have found that the HPLC type sample analyzer may be constituted by the gradient liquid feed device, a sample injection device configured to inject a sample into a carrier liquid flow path provided on a downstream side of the mixer of the gradient liquid feed device, a column device which is arranged in a carrier liquid flow path provided on a downstream side of the sample injection device and configured to separate components of the sample, and a detection device which is arranged in a carrier liquid flow path provided on a downstream side of the column device and configured to detect components of the sample.

Effects of the Invention

According to the present invention, the responsiveness of a gradient can be improved by employing a linear high-pressure gradient system by using a plurality of pumps which respectively correspond to the plurality of carrier liquids. In addition to this, by using a single plunger pump as the pump, the size of the gradient liquid feed device can be reduced. In addition, the pulsation that may occur during liquid feeding when a single plunger pump is used can be eliminated when a pulse damper is used, the single plunger pump includes a function for variably setting the length of stroke for drawing and discharging the carrier liquid, and the single plunger pump includes a function for variably setting a ratio between carrier liquid drawing time and carrier liquid discharge time.

More specifically, because the length of strokes for drawing and discharging the carrier liquid is variable, the flow rate can be changed without changing the cycle time of plunger reciprocating motions. Pulsation can be suppressed because the number of cycle time of reciprocating motion can be secured so that effects from pulsation can be decreased during liquid feeding at a low flow rate. Note that a conventional technique of changing the flow rate, in which the speed of reciprocating motion of a plunger is changed, can be used in combination with the present invention.

In addition, because the ratio between carrier liquid drawing time and carrier liquid discharge time is variable, time taken for a drawing step can be freely set when the speed of reciprocating motion of the plunger is changed in accordance with the flow rate, and accordingly, pulsation can be suppressed. Furthermore, the composition of a carrier liquid can be suitably changed.

Furthermore, by combining the function for variably setting the length of strokes for drawing and discharging the carrier liquid and the function for variably setting the ratio between carrier liquid drawing time and carrier liquid discharge time, the plunger can be operated under conditions suitable for suppressing pulsation by combining freely chosen drawing time and discharge time, the freely chosen speed of plunger reciprocating motions, and the freely chosen cycle time of plunger reciprocating motions together.

As a result, a low-cost, small-size linear high-pressure gradient liquid feed device can be provided.

Accordingly, by configuring the HPLC type sample analyzer by using the gradient liquid feed device, analysis can be carried out with high accuracy and at high speed while contributing to the reduction in size of HPLC type sample analyzers at the same time.

BRIEF DESCRIPTION OF THE DRAWING

FIG. 1 is a system diagram of an HPLC type sample analyzer which includes a gradient liquid feed device illustrated as an embodiment of the present invention.

MODE FOR CARRYING OUT THE INVENTION

An embodiment of the present invention will be described below.

FIG. 1 is a system diagram of an embodiment of the present invention, in which the valve according to Japanese Patent Application No. 2013-148183 (PCT/JP2014/61256) is used as a valve 16.

The HPLC type sample analyzer according to the present embodiment is used to analyze various types of subjects to be analyzed that can be analyzed on the technique of HPLC, e.g., components of hemoglobin in blood including hemoglobin A1c.

To the HPLC type sample analyzer illustrated in FIG. 1, carrier liquid reservoir tanks 51,52 for storing a first carrier liquid and a second carrier liquid (eluent) of different composition, including the concentration of a separation solvent, for example, and a diluting and washing liquid reservoir tank 53 are connected via a common deaeration device 54. Note that the first and the second carrier liquid reservoir tanks 51,52 and the diluting and washing liquid reservoir tank 53 may be designed into a kit as a reagent kit 50. In addition, the diluting and washing liquid reservoir tank 53 may be divided into separated reservoir tanks, i.e., into a diluting liquid reservoir tank 53a and a washing liquid reservoir tank 53b.

The HPLC type sample analyzer illustrated in FIG. 1 is constituted by liquid feed pumps 1,2 for feeding the first and the second carrier liquid from the reservoir tanks 51,52, a mixer 3 for mixing the carrier liquid fed from the liquid feed pumps 1,2, a pulse damper 4 which is in communication with the mixer 3 and configured to absorb pulsation that may occur during liquid feeding, a flow path 5 in which the carrier liquid from the mixer 3 flows, a sample injection device 6 to which the flow path 5 is connected at an inlet port thereof, a flow path 7 in which the carrier liquid flows and connected to the sample injection device 6 at an outlet port thereof, a column device 8 and a detection device 9 arranged in the flow path 7, and a drain flow path 10 disposed on a downstream side thereof.

The liquid feed pumps 1,2 are each a single plunger pump, and include check valves (one-way valves) 61 to 64 at their drawing ports and discharge ports of a cylinder chamber (pump chamber), respectively, of which the volume is changed by the plunger. In addition, the liquid feed pumps 1,2 are a variable volume type pump of which the discharge volume can be changed by changing the stroke of the plunger, and thus, the flow rate ratio between the two liquid feed pumps 1,2 can be changed.

In the gradient liquid feed device according to the present invention, the valve according to Japanese Patent Application No. 2013-148183 (PCT/JP2014/61256) is used, and because the pipes for bringing the cylinder chamber of the single plunger pump and the measuring pump into mutual communication are provided, air in the cylinder chamber can be released even when the length of strokes of drawing and discharging the carrier liquid from the single plunger pump is short.

The mixer 3 mixes the first carrier liquid from the liquid feed pump 1 and the second carrier liquid from the liquid feed pump 2 for homogenization. Specifically, the mixer 3 introduces two types of carrier liquids into a cylindrical container in a tangential direction to mix them together, and causes the mixed solution to be led in the axial direction. Accordingly, by changing the flow rate ratio between the liquid feed pumps 1,2 and by mixing the carrier liquids by using the mixer 3, a carrier liquid having freely selected concentration at a level between the concentration of the first carrier liquid and that of the second carrier liquid (a gradient function) can be obtained. Note that a pipe 19 is connected to the mixer 3, which is a pipe used for carrying out air bleeding and filling of the carrier liquid at the stage of preparation for operation of the sample analyzer. The pipe 19 is closed by the switching valve 16, which will be described later below, during a normal operation.

The pulse damper 4 is a diaphragm type damper that is in communication with a space within the mixer 3, and absorbs pulsations that may occur due to the use of a single plunger pump as the liquid feed pumps 1,2 particularly for reducing the size of the sample analyzer. The pulse damper 4 may be provided with a pressure sensor. Note that the pulse damper 4 is installed in a flow path which is in communication with the mixer 3, and at least one pulse damper 4 is installed in a flow path between the mixer 3 and the sample injection device 6, in a flow path between the mixer 3 and the switching valve 16, in a flow path between the mixer 3 and the liquid feed pump 1, or in a flow path between the mixer 3 and the liquid feed pump 2. It is preferable that at least one pulse damper 4 be installed in the flow path between the mixer 3 and the liquid feed pump 1 or in the flow path between the mixer 3 and the liquid feed pump 2 because the responsiveness of the gradient can be improved with this configuration.

Note that the single plunger pump used as the liquid feed pumps 1,2 can increase the number of times of discharge operations per unit liquid feed amount by using a small-volume pump therefor, decrease the amount of discharge for one operation by decreasing the stroke of the plunger as the flow rate becomes low, and further suppress pulsation that may occur during liquid feeding by changing a ratio between the drawing time and the discharge time. Furthermore, due to the action by the mixer 3 and the pulse damper 4, the liquid feeding can be carried out with substantially low pulsation.

For the capacity of the single plunger pump for causing the gradient liquid feed device of the present invention to deliver its performance, the gradient liquid feed device may be provided with a variable stroke setting function within a range required for a single plunger pump for analytic chemistry. For example, the single plunger pump may be respectively provided with the variable stroke setting function within the following ranges:

range of flow rate: 1 µL/min to 10 mL/min,
range of plunger stroke: 0.01 mm to 20 mm, and
range of plunger volume: 0.1 µL to 100 µL.

In addition, it is preferable that the ratio between the drawing time and the discharge time be variable, that control be performed so that the ratio of the drawing time is decreased while the discharge time is increased as the flow rate becomes lower, and that the carrier liquid drawing time be an extremely short time during liquid feeding at a low flow rate. Note that the term "plunger volume" herein refers to the volume of the space formed by the plunger and the cylinder chamber.

For an apparatus for measuring hemoglobins in blood including a value of hemoglobin A1c for diabetes testing, the gradient liquid feed device of the present invention includes, for example, a single plunger pump that satisfies a preferable range of flow rate of 10 µL/min to 1.5 µL/min, a preferable range of plunger stroke of 0.1 mm to 2.21 mm, and a preferable range of plunger volume of 0.8 µL to 17.5 µL can be illustrated as an example. Furthermore, an example of the ratio between the drawing time and the discharge time can be a ratio of 1:1 when the flow rate is at the maximum, and it is preferable for control to be performed so that the ratio of the drawing time is decreased while the ratio of the discharge time is increased as the flow rate becomes lower and for the carrier liquid drawing time to be an extremely short time during liquid feeding at a low flow rate. As the ratio between the drawing time and the discharge time when the flow rate is low, a ratio of 1:1,000 can be illustrated as an example.

The sample injection device (main body) 6, for which the detailed description of its configuration is omitted here, includes a sample injection portion 22. The sample injection portion 22 is disposed between the flow path 5 for feeding the carrier liquid from the mixer 3 and the flow path 7 disposed on the downstream side thereof and is capable of injecting a sample into the carrier liquid by using the needle 27 by moving the needle 27 to a sample injection position by ascending and descending motions of a needle moving device (not illustrated).

In addition, the sample injection device 6 includes a sample drawing portion (vessel holding portion) 39 arranged below the sample injection portion 22. The sample drawing portion 39 can draw the sample by using the needle 27 by moving the needle 27 to a sample drawing position. Accordingly, the sample drawn by the sample drawing portion 39 is to be injected into the carrier liquid in the sample injection portion 22. Note that the drawing and the injection are carried out after connecting a measuring pump (sampling pump) 11 to a pipe 12 to the needle 27 via the switching valve 16.

In addition, the sample injection device 6 is provided with a washing portion 33 for washing the needle 27, which portion being formed integrally with a housing of the sample injection portion 22 and arranged at a location between the sample injection portion 22 and the sample drawing portion 39. The washing portion 33 supplies a washing liquid to the needle 27 that has been moved to a washing position to carry out washing of the needle 27. The washing is carried out after connecting the measuring pump 11 to a pipe 13 from the diluting and washing liquid reservoir tank 53 via the switching valve 16 and drawing the washing liquid and then connecting the measuring pump 11 to the pipe 12 to the needle 27 via the switching valve 16. After the washing, the washing liquid is recovered by using a drain pump (waste pump) 14 and is then discharged into a drain flow path 15.

The column device 8 is disposed in the carrier liquid flow path 7 arranged on a downstream side of the sample injection device 6, and separates the components contained in the sample from each other.

The detection device 9, which is disposed on the downstream side of the column device 8, detects the separated component and transmits a signal of the detected component to a data processing device (not illustrated). Results of the data processing by the data processing device are output as analysis results.

A control device 30 controls the liquid feed pumps 1,2, the sample injection device 6, the detection device 9, the measuring pump 11, the drain pump 14, and the switching valve 16. Particularly for gradient liquid feeding, the control device 30 controls the liquid feed pumps 1,2 for the length of stroke, the ratio between the drawing time and the discharge time, the speed of the plunger reciprocating motion, the cycle time of the reciprocating motion of the plunger, and the like. In addition, when the pulse damper 4 is provided with a pressure sensor, a signal from the pressure sensor is input to the control device 30. The control device 30 includes a computer and a recording medium, in which various types of programs are previously recorded.

The sample analyzer illustrated in FIG. 1 is provided with the switching valve 16, which can be positioned at either one of four positions a to d. The four positions a to d correspond to ports a to d, respectively, and a first in-valve flow path 16a, which is in communication with the measuring pump 11, is selectively connected to one of the ports a to d when the first in-valve flow path 16a is turned. In addition, another arc-like second in-valve flow path 16b is turned in accordance with the turning of the first in-valve flow path 16a, and the ports e and f are brought into communication with each other due to this motion of the arc-like second in-valve flow path 16b at the positions a and b. Note that the in-valve flow paths 16a,16b are formed on a rotor of the switching valve 16 while the ports a to f are formed on a stator of the switching valve 16.

The port a is connected to a cylinder chamber of the liquid feed pump 1 via a pipe 17 for bleeding of air and filling of the carrier liquid.

The port b is connected to the cylinder chamber of the liquid feed pump 2 via a pipe 18 for bleeding of air and filling of the carrier liquid.

The port c is connected to the needle 27 via the pipe 12.

The port d is connected to the diluting and washing liquid reservoir tank 53 via the pipe 13.

The port e is connected to the pipe 19 from the mixer 3 for bleeding of air and filling of the carrier liquid, and the port f is connected to a drain flow path 20.

In other words, the rotor of the switching valve 16 is provided with a center pipe connection port at which the measuring pump 11 is connected, the first in-valve flow path 16a which is in communication with the center pipe connection port, and the arc-like second in-valve flow path 16b which turns in accordance with the turning of the first in-valve flow path 16a.

The stator of the switching valve 16 is provided with a first pipe connection port group including the above-described ports a to d, and a second pipe connection port group including the above-described ports e and f.

The first pipe connection port group (the ports a to d) is in communication with the center pipe connection port via the first in-valve flow path 16a independently from one another in accordance with the turning of the first in-valve flow path 16a, and the positions of connection between the first in-valve flow path 16a and each of the ports a to d exist on the same circumference.

The second pipe connection port group (the ports e and f) can be brought into communication with each other via the arc-like second in-valve flow path 16b in accordance with the turning of the arc-like second in-valve flow path 16b. The positions of connection between the arc-like second in-valve flow path 16b and each of the ports e and f exist on the circumference that is coaxial with the circumference on which the ports a to d exist, of which the diameter is different from that of the circumference on which the ports a to d exist.

At the ports a and b of the first pipe connection port group, the two ports e and f of the second pipe connection port group are brought into communication by the arc-like second in-valve flow path 16b when the center pipe connection port is brought into communication with the port a or b.

At the other ports c and d among the first pipe connection port group, the two ports e and f of the second pipe connection port group are not brought into mutual communication via the arc-like second in-valve flow path 16b when the center pipe connection port is brought into communication with the port c or d.

The air bleeding and the filling of the carrier liquid will be described below, which is carried out at the stage of preparation of operation of the sample analyzer illustrated in FIG. 1.

At the stage of preparation for the operation, the following operations are carried out in an automatic operation mode to fill the inside of the flow path with the liquid by releasing air from the inside of the flow path.

The position of the switching valve 16 is switched to the position a (the state illustrated in FIG. 1). At the position a, the measuring pump 11 is connected to the port a (the pipe 17) and the port e and the port f are brought into communication with each other.

In this state, first, the measuring pump 11 carries out the drawing operation. Then, the first carrier liquid in the reservoir tank 51 is fed through the check valve 61 on the drawing side of the liquid feed pump 1, then through the pipe 17 from the cylinder chamber of the liquid feed pump 1 to be drawn into the measuring pump 11. In this manner, the flow paths from the reservoir tank 51 to the liquid feed pump 1 are filled with the carrier liquid.

Next, the measuring pump 11 carries out the discharge operation. Then the first carrier liquid is pumped from the measuring pump 11 into the liquid feed pump 1 via the pipe 17, and the check valve 62 on the discharge side is opened to allow the carrier liquid flow to be fed into the mixer 3. Furthermore, the carrier liquid is then allowed to flow into the pipe 19 from the mixer 3 due to the resistance force from the column device 8, and it is further discharged from the pipe 19 as a drain through the drain flow path 20 connected to the pipe 19 via the switching valve 16 (the ports e and f).

Next, the switching valve 16 is allowed to turn clockwise by 60° to position the switching valve 16 at the position b. At the position b, the measuring pump 11 is brought into communication with the port b (the pipe 18) and the ports e and f continue their mutual communication.

In this state, first, the measuring pump 11 carries out the drawing operation. Then the second carrier liquid in the reservoir tank 52 is fed through the check valve 63 on the drawing side of the liquid feed pump 2, then is fed from the cylinder chamber of the liquid feed pump 2, to be drawn into the measuring pump 11 through the pipe 18. In the above-described manner, the flow paths from the second carrier liquid reservoir tank 52 to the liquid feed pump 2 are filled with the carrier liquid.

Next, the measuring pump 11 carries out the discharge operation. Then the second carrier liquid in the measuring pump 11 is pumped into the liquid feed pump 2 via the pipe 18, then the check valve 64 on the discharge side is opened to allow the carrier liquid to flow into the mixer 3. Furthermore, the carrier liquid is then allowed to flow into the pipe 19 from the mixer 3 due to the resistance force from the column device 8, and is further discharged from the pipe 19 as a drain through the drain flow path 20 connected to the pipe 19 via the switching valve 16 (the ports e and f).

Next, the switching valve 16 is moved to a position other than the positions a and b to start the feeding from the liquid feed pumps 1,2 and fill the carrier liquid flow paths 5 and 7 including the sample injection portion 22 and the column device 8 and the detection device 9 with the carrier liquid.

A dilution step, a sample drawing step, a sample injection step, and a washing step carried out during a normal operation state of the sample analyzer illustrated in FIG. 1 will be described below.

In the dilution step, the needle 27 is positioned at a sample drawing position (the sample drawing portion 39), i.e., at a position in an inside of a vessel containing the sample.

For the position of the switching valve 16, the switching valve 16 is positioned at the position d first. At the position d, the measuring pump 11 is connected to the port d (the pipe 13). In this state, the measuring pump 11 carries out the drawing operation. Then the diluent (the diluting and washing liquid) in the reservoir tank 53 is drawn into the measuring pump 11 via the pipe 13.

Next, the position of the switching valve 16 is changed to the position c. At the position c, the measuring pump 11 is connected to the port c (the pipe 12). In this state, the measuring pump 11 carries out the discharge operation. Then the diluent in the measuring pump 11 is pumped into the needle 27 via the pipe 12. The needle 27 is positioned at the sample drawing position (the sample drawing portion 39), i.e., at a position inside the vessel, and thus, the diluent is supplied into the vessel. The measuring pump 11 repeats the drawing operation and the discharge operation, and thus, the needle 27 draws and returns the mixed solution including the sample and the diluent in the vessel, and thereby the mixed solution in the vessel is stirred and the sample is homogeneously diluted.

In the sample drawing step, the needle 27 is positioned at the sample drawing position (the sample drawing portion 39), i.e., at a position inside the vessel containing the sample (the sample diluted with the diluent).

The position of the switching valve 16 is set to the side of the needle 27 (the position c) and the measuring pump 11 is connected to the pipe 12. In this state, the measuring pump 11 carries out the drawing operation. Then, the sample in the vessel is drawn into the needle 27.

In the sample injection step, the needle 27 is positioned at the sample injection position (the sample injection portion 22).

The position of the switching valve 16 is set to the side of the needle 27 (the position c) and the measuring pump 11 is connected to the pipe 12. In this state, the measuring pump 11 carries out the discharge operation. Then the sample in the needle 27 is injected into the sample injection portion 22 arranged between the carrier liquid flow paths 5 and 7.

In the washing step, the needle 27 is positioned at a washing position (not illustrated).

The position of the switching valve 16 is set to the position d first. At the position d, the measuring pump 11 is connected to the port d (the pipe 13). In this state, the measuring pump 11 carries out the drawing operation. Then, the washing liquid (the diluting and washing liquid) in the reservoir tank 53 is drawn into the measuring pump 11 via the pipe 13.

Next, the position of the switching valve 16 is set to the position c. At the position c, the measuring pump 11 is connected to the port c (the pipe 12). In this state, the measuring pump 11 carries out the discharge operation. Then the washing liquid in the measuring pump 11 is pumped into the needle 27 via the pipe 12. The needle 27 is positioned at the washing position, and the needle 27 is washed with the washing liquid there. After the washing, the washing liquid is recovered by the drain pump 14 and is then discharged through the drain flow path 15 as a drain. In this step, because the flow rate of the drain pump 14 is higher than the flow rate of the measuring pump 11, the washing liquid after the washing is discharged from the drain flow path 15 together with the air that entered through a guide hole (not illustrated) of the needle 27 without any leakage to the outside. The washing liquid is mixed with air to take the form of a mist, and thereby, the efficiency of the washing can be increased, the consumption of the washing liquid can be reduced, and accordingly, the washing of the needle 27 can be suitably carried out.

The flow of the carrier liquid during the normal operation of the sample analyzer illustrated in FIG. 1 will be described below.

The liquid feed pumps (single plunger pumps) 1,2 are driven, and the flow rate ratio of the two liquid feed pumps 1,2 is varied with time. The first carrier liquid from the liquid feed pump 1 and the second carrier liquid from the liquid feed pump 2 are mixed together to be homogenized, and the pulsation is absorbed by the pulse damper 4.

The flow rate ratio between the liquid feed pumps 1,2 is changed, the mixer 3 mixes the carrier liquids together, and the pulse damper 4 absorbs the pulsation as described above, and thus a carrier liquid of freely selected concentration of a level between the concentration of the first carrier liquid and that of the second carrier liquid can be obtained.

The mixed carrier liquid is fed to the sample injection portion 22 via the flow path 5, and a sample, e.g., blood or the like that has been diluted and hemolyzed, is injected into the carrier liquid there. The carrier liquid including the injected sample is fed to the column device 8 and then to the detection device 9 via the flow path 7. In the column device 8, a specific component is separated from the sample. In the detection device 9 arranged on the downstream side of the column device 8, the separated component (e.g., a hemoglobin component such as hemoglobin A1c) is detected by a detection method such as determination of absorbance.

An exemplary operation of the pump performed during gradient liquid feeding will be described with reference to a case in which a measuring apparatus for measuring hemoglobins in blood for diabetes testing is used.

Cases in which a gradient is made will be described in which the total flow rate (the sum of the flow rate of the pump 1 and the flow rate of the pump 2) is maintained at a specific value such as 1 mL/min.

When the liquid feeding from the pump 1 is carried out at the highest flow rate while the pump 2 is stopped, then the length of the stroke of the plunger of the pump 1 is controlled to be a length in accordance with the highest flow rate and the ratio between the drawing time and the discharge time is controlled to be substantially 1:1.

Next, a case in which the flow rate of the pump 1 is decreased when the liquid feeding from the pump 2 is started will be described. The control is carried out so that as the flow rate of the pump 1 is decreased, the length of stroke of the plunger of the pump 1 is decreased and the ratio of the drawing time is decreased while the ratio of the discharge time is increased. On the other hand, the control is performed when the liquid feeding from the pump 2 is performed at a flow rate around a lowest flow rate that can be set, so that the length of stroke of the plunger of the pump 2 becomes short, that the carrier liquid drawing time becomes extremely short, and that the carrier liquid discharge time becomes long.

The increase and the decrease of the flow rate can be controlled by adjusting the rotation frequency of the pump, the length of the stroke of the plunger, and the like. The control can be performed according to a combination of these parameters.

The increase and the decrease of the carrier liquid drawing time and the carrier liquid discharge time can be controlled by adjusting the length of the stroke of the plunger, by changing the ratio between the drawing time and the discharge time within a certain cycle time of the reciprocating motion, and the like. The control can be performed according to a combination of these parameters.

A case in which the flow rate of the pump 1 is further decreased while the flow rate of the pump 2 is increased will be described.

The control is performed when the liquid feeding from the pump 1 is performed at a flow rate around a lowest flow rate that can be set, so that the length of stroke of the plunger of the pump 1 becomes short, that the carrier liquid drawing time becomes an extremely short time, and that the carrier liquid discharge time becomes long. The control is carried out so that as the flow rate of the pump 2 is increased, the length of stroke of the plunger of the pump 2 is increased and that the ratio of the drawing time is increased while the ratio of the discharge time is decreased.

When the liquid feeding from the pump 2 is carried out at the highest flow rate while the pump 1 is stopped, then the length of the stroke of the plunger of the pump 2 may be controlled to be a length in accordance with the highest flow rate and the ratio between the drawing time and the discharge time may be controlled to be substantially 1:1.

In liquid feeding using a cam type plunger pump, conventional techniques have a problem of increasing effect from pulsation that may occur due to the long drawing time taken during liquid feeding at a low flow rate. However, by controlling the pump 1 and the pump 2 in the above-described manner, the carrier liquid drawing time can be shortened to an extremely short time even during liquid feeding at a low flow rate. To paraphrase this, the time in which the flow velocity for the carrier liquid becomes slow can be shortened to an extremely short time.

The length of stroke of the plunger and the ratio between the carrier liquid drawing time and the carrier liquid discharge time are variably controlled as described above, and thereby it is enabled to suppress the effect from pulsation even during liquid feeding at a low flow rate. By using the pump and the pulse damper described above that operate in the above-described manner in combination, the liquid feeding can be carried out with substantially low pulsation.

The gradient liquid feed device according to the present embodiment is constituted by a plurality of carrier liquid reservoir tanks 51,52 configured to store carrier liquids of mutually different compositions, a plurality of single plunger pumps (liquid feeding pumps) 1,2 capable of drawing and discharging the carrier liquid from the plurality of carrier liquid reservoir tanks 51,52, the mixer 3 configured to mix the carrier liquids fed from the plurality of single plunger pumps 1,2 and feed the mixed carrier liquid, and the pulse damper 4 in communication with the mixer 3 and configured to absorb pulsation, and in the gradient liquid feed device, the single plunger pumps 1,2 have the function for variably setting the length of stroke for drawing and discharging the carrier liquid and further a function for variably setting the ratio between the carrier liquid drawing time and the carrier liquid discharge time, and thereby the following effects can be achieved.

By employing the linear high-pressure gradient system which uses the plurality of pumps corresponding to the respective plurality of carrier liquids, the responsiveness of gradient can be improved. In addition, by using the single plunger pumps 1,2 as the pumps, the size of the gradient liquid feed device can be reduced. In addition, the pulsation that may occur during liquid feeding when the single plunger pumps 1,2 are used can be eliminated when the pulse damper is used, the single plunger pumps include a function for variably setting the length of stroke for drawing and discharging the carrier liquid, and the single plunger pumps include the function for variably setting the ratio between the carrier liquid drawing time and the carrier liquid discharge time. As a result, the small-size, low-cost linear high-pressure gradient liquid feed device can be provided.

In addition, in the gradient liquid feed device according to the present embodiment, the center pipe connection port of the switching valve 16 including the following (A) to (C) is connected to the measuring pump 11 via the switching valve 16, and the gradient liquid feed device includes pipes 17,18 for bringing the measuring pump 11 into communication with the cylinder chambers of the single plunger pumps 1,2 by bringing at least one pipe connection port of the first pipe connection port group into communication with the cylinder chambers of the single plunger pumps 1,2.

(A) A rotor which includes the following (1) to (3):
(1) at least one center pipe connection port;
(2) at least one first in-valve flow path which is in communication with the center pipe connection port; and
(3) at least one arc-like second in-valve flow path which turns in accordance with the turning of the first in-valve flow path and have a flow path length equal to or greater than a distance traveled by one motion of the turning.

In the present embodiment, one center pipe connection port, one first in-valve flow path 16a, and one arc-like second in-valve flow path 16b are provided.

(B) A stator which includes the following (4) and (5):

(4) a first pipe connection port group having at least two pipe connection ports independently in communication with the center pipe connection port via the first in-valve flow path 16a when the first in-valve flow path 16a of the rotor turns and of which connection positions exist on one circumference around a center axis of the rotor.

In the present embodiment, four pipe connection ports a, b, c, and d that are to be brought into communication independently from one another with the center pipe connection port are provided.

(5) A second pipe connection port group having positions of connection with the arc-like second in-valve flow path 16b on a circumference of a circle which is coaxial in relation to and having a diameter different from the circumference on which positions of connection between the first in-valve flow path 16a of the rotor and the first pipe connection port group (a,b,c,d) exist, the second pipe connection port group having at least two pipe connection ports that are to be brought into mutual communication when the arc-like second in-valve flow path 16b is turned.

In the present embodiment, two pipe connection ports e,f that are to be brought into mutual communication when the arc-like second in-valve flow path 16b is turned are provided.

(C) An arrangement of the rotor and the stator satisfies the following relationships (6) and (7):

(6) At at least one of the pipe connection ports, of the first pipe connection port group of the stator that is brought into communication independently with the first in-valve flow path 16a of the rotor, when the center pipe connection port and the pipe connection port are brought into mutual communication, at least two mutually adjacent pipe connection ports of the second pipe connection port group are brought into mutual communication via the arc-like second in-valve flow path 16b.

In the present embodiment, the pipe connection ports e,f are brought into mutual communication via the arc-like second in-valve flow path 16b when the center pipe connection port and the pipe connection port a or b are brought into mutual communication.

(7) At the other pipe connection ports of the first pipe connection port group, when the center pipe connection port and the pipe connection port are brought into mutual communication, the mutually adjacent pipe connection ports of the second pipe connection port group are not to be brought into mutual communication via the arc-like second in-valve flow path 16b.

In the present embodiment, the pipe connection ports e,f are not to be brought into mutual communication via the arc-like second in-valve flow path 16b when the center pipe connection port and the pipe connection port c or d are brought into mutual communication.

With the above-described configuration, the air bleeding described above can be performed. Note that for the arc-like second in-valve flow path described in the above item (3), a preferable flow path length is equal to or greater than a distance traveled by one motion of the turning, and a more preferable flow path length thereof is a length equal to or greater than a distance traveled by two motions of the turning.

In addition, the HPLC type sample analyzer according to the present embodiment is constituted by the gradient liquid feed device; the sample injection device 6 configured to inject a sample into the carrier liquid flow path 5 provided on a downstream side of the mixer 3 of the gradient liquid feed device; the column device 8 arranged on the carrier liquid flow path 7 provided on a downstream side of the sample injection device 6 and configured to separate components of the sample; and the detection device 9 arranged on a carrier liquid flow path provided on a downstream side of the column device 8 and configured to detect components of the sample, and thereby, it is enabled to perform an analysis with high accuracy and high speed.

In addition, by using the HPLC type sample analyzer which injects blood into the carrier liquid flow path as the sample, separates and detects hemoglobin components of the blood, and measures the amounts of the components detected (hemoglobin A1c values and the like), the present embodiment can contribute to improving the accuracy and the speed of diabetes testing.

Note that in the descriptions above, an example of the gradient is described with reference to the case in which the mixture ratio of the two carrier liquids of which the concentrations of the separation solvent are mutually different is changed to change the concentration of the separation solvent. However, the present embodiment is not limited to this, and the mixture ratio of a plurality of two types or more carrier liquids of mutually different compositions may be changed to change the composition of the carrier liquid.

The embodiment described above with reference to the drawing is merely an example of the present invention, and the present invention can of course include not only the invention directly illustrated by the embodiment described above, but also various alterations and modifications made by one skilled in the art within the scope of the present invention as claimed in the claims.

INDUSTRIAL APPLICABILITY

The gradient liquid feed device according to the present invention can be suitably used, together with the HPLC type sample analyzer that uses the gradient liquid feed device, for sample analyses by HPLC methods such as diabetes testing, and therefore, it highly industrially applicable.

REFERENCE SYMBOL LIST

1 First liquid feed pump (single plunger pump)
2 Second liquid feed pump (single plunger pump)
3 Mixer
4 Pulse damper
5 Carrier liquid flow path
6 Sample injection device
7 Carrier liquid flow path
8 Column device
9 Detection device
10 Drain flow path
11 Measuring pump (Sampling pump)
12 Pipe
13 Pipe
14 Drain pump (Waste pump)
15 Drain flow path
16 Switching valve
16a First in-valve flow path
16b Second in-valve flow path
17 to 19 Pipe
20 Drain flow path 22 Sample injection portion
27 Needle
30 Control device
33 Washing portion
39 Sample drawing portion (vessel holding portion)
50 Reagent kit
51 First carrier liquid reservoir tank
52 Second carrier liquid reservoir tank
53 Diluting and washing liquid reservoir tank
54 Deaeration device
61 to 64 Check valve

The invention claimed is:

1. A gradient liquid feed device used for high performance liquid chromatography, comprising:
   a plurality of carrier liquid reservoir tanks configured to store carrier liquids of mutually different compositions;
   a plurality of single plunger pumps capable of drawing and discharging a carrier liquid from respective carrier liquid reservoir tanks;
   a mixer configured to mix the carrier liquids discharged from the plurality of single plunger pumps together and feed the mixed carrier liquid;
   a pulse damper in communication with the mixer and configured to absorb pulsation that may occur during liquid feeding, and
   a switching valve and a measuring pump, the measuring pump being connected to a center pipe connection port of the switching valve, the switching valve including the following (A) to (B):
   (A) a plurality of in-valve flow paths including the following (1) and (2):
   (1) at least one first in-valve flow path which is in communication with the center pipe connection port; and
   (2) at least one arc-like second in-valve flow path;
   (B) a plurality of pipe connection port groups including the following (3) and (4):
   (3) a first pipe connection port group having at least two pipe connection ports independently in communication with the center pipe connection port via the first in-valve flow path and each being in communication with a cylinder chamber of a respective one of the plurality of single plunger pumps via a pipe, the first in-valve flow path being rotatable relative to the at least two pipe connection ports of the first pipe connection port group so as to independently communicate with the at least two pipe connection ports and respective pipes thereof upon relative rotation of the first in-valve flow path; and
   (4) a second pipe connection port group having positions of connection with the arc-like second in-valve flow path, the arc-like second in-valve flow path being rotatable relative to the second pipe connection port group, the second pipe connection port group having first and second pipe connection ports that are positioned on a circumference of a circle so as to be in mutual communication with the arc-like second in-valve flow path and with each other when the arc-like second in-valve flow path is in a first position, the first pipe connection port being in communication with a pipe that communicates with a device discharge, and the second pipe connection port being in communication with a pipe that communicates with the mixer,
   wherein each of the plurality of single plunger pumps includes at least one of a function for variably setting a length of stroke for drawing and discharging the carrier liquid and a function for variably setting a ratio between carrier liquid drawing time and carrier liquid discharge time.

2. The gradient liquid feed device according to claim 1, wherein at least one pulse damper is installed in a flow path provided between one of the plurality of single plunger pumps and the mixer.

3. The gradient liquid feed device according to claim 1, wherein for each of the single plunger pumps, a range of flow rate is 1 µL/min to 10 mL/min, a range of stroke of a plunger is 0.01 mm to 20 mm, and a range of a volume of the plunger is 0.1 µL to 100 µL.

4. A high performance liquid chromatography type sample analyzer comprising:
   the gradient liquid feed device according to claim 1, wherein the analyzer includes:
   (1) a sample injection device configured to inject a sample into a carrier liquid flow path provided on a downstream side of the mixer;
   (2) a column device which is arranged in the carrier liquid flow path provided on a downstream side of the sample injection device and configured to separate components of the sample; and
   (3) a detection device which is arranged in the carrier liquid flow path provided on a downstream side of the column device and configured to detect components of the sample.

5. A hemoglobin component measurement method that uses the gradient liquid feed device according to claim 1, wherein blood is injected into the carrier liquid flow path as the sample, hemoglobin components of the blood are separated and detected, and the amounts of the components detected are measured.

* * * * *